Figure 2:
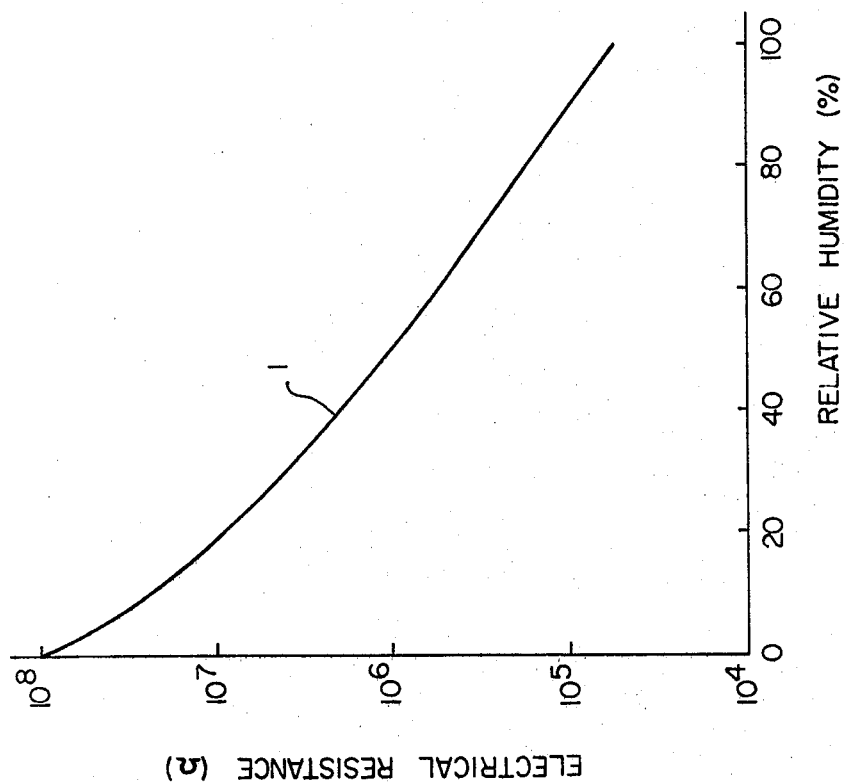

United States Patent [19]

Nitta et al.

[11] 4,086,556
[45] Apr. 25, 1978

[54] HUMIDITY SENSITIVE CERAMIC RESISTOR

[75] Inventors: Tsuneharu Nitta, Katano; Ziro Terada, Yao; Shigeru Hayakawa, Hirakata, all of Japan

[73] Assignee: Matsushita Electric Industrial Co., Ltd., Japan

[21] Appl. No.: 720,078

[22] Filed: Sep. 2, 1976

[30] Foreign Application Priority Data

| Sep. 18, 1975 | Japan | 50-113320 |
| Sep. 30, 1975 | Japan | 50-118368 |
| Sep. 30, 1975 | Japan | 50-118369 |
| Sep. 30, 1975 | Japan | 50-118370 |
| Sep. 30, 1975 | Japan | 50-118371 |

[51] Int. Cl.$^2$ .............................................. H01L 7/00
[52] U.S. Cl. ...................................... 338/35; 252/518; 252/519; 252/520; 252/521; 338/34
[58] Field of Search .................... 338/34, 35; 252/512, 252/518.1, 519, 520, 521; 106/73.5, 73.3, 39.5

[56] References Cited

U.S. PATENT DOCUMENTS

| 3,766,098 | 10/1973 | Masuyama et al. | 252/519 |
| 3,926,858 | 12/1975 | Ichinose et al. | 252/519 |

Primary Examiner—Benjamin R. Padgett
Assistant Examiner—Josephine L. Barr
Attorney, Agent, or Firm—Wenderoth, Lind & Ponack

[57] ABSTRACT

There is provided a humidity sensitive ceramic resistor having high humidity activity, low electrical resistance, quick response rate to humidity and high stability with respect to time, temperature, humidity and electric load which is suited for humidity-controlling devices. The ceramic resistor comprises a ceramic composition comprising at least one component having a spinel type cubic symmetry selected from the group consisting of $MgCr_2O_4$, $FeCr_2O_4$, $NiCr_2O_4$, $CoCr_2O_4$, $MnCr_2O_4$, $CuCr_2O_4$, $Mg_2TiO_4$, $Zn_2TiO_4$, $Mg_2SnO_4$ and $Zn_2SnO_4$, and, if desired, at least one component selected from the group consisting of $TiO_2$, $ZrO_2$, $HfO_2$ and $SnO_2$.

30 Claims, 4 Drawing Figures

HUMIDITY SENSITIVE CERAMIC RESISTOR

This invention relates to a humidity sensitive resistor, and more particularly to a novel humidity sensitive ceramic resistor comprised of a semiconductive ceramic composition.

Recently, the electronic industry has required humidity sensitive semiconductors suitable for making humidity controlling devices operating over a wide range of relative humidity i.e. from 0 percent to 100 percent. It is important in making such devices, that the humidity sensitive materials have high humidity activity, low electrical resistance, and small variation of these characteristics with time.

In the prior art, there are known humidity sensitive semiconductive materials such as magnetite, germanium, selenium, potassium metaphosphate or the like. However, the conventional materials such as magnetite, germanium and selenium have a disadvantage that their response rate to humidity is very slow. For example, a magnetite thin film needs about two minutes to respond to a change of relative humidity from 60% to 98%. On the other hand, while potassium metaphosphate thin film responds in about two seconds to a change of relative humidity from 80% to 33%, it has a disadvantage in that the characteristics thereof vary greatly with lapse of time. Further, these conventional humidity sensitive resistors also have other disadvantages such as a narrow range of relative humidity to which the resistors can respond, lack of uniformity of characteristics, high cost, etc.

In contrast to such known semiconductive materials, there are also known humidity sensitive resistors comprising metal oxide ceramic materials such as $Al_2O_3$, $Cr_2O_3$, NiO and the like, having a very quick response to humidity, and they have advantages in that they can be easily formed into a desired shape in mass production. However, these conventional ceramic materials usually have a high electrical resistance, e.g. above $10^{13}\Omega$ at 0 percent relative humidity, and they are not suitable for low humidity sensitive resistors. For example, a humidity resistor of $Al_2O_3$ or $Cr_2O_3$ covers a narrow range of relative humidity from 80% to 100% with variations of electrical resistance from 1000 MΩ to 1 MΩ. In addition, these ceramic materials undesirably have a hysteresis characteristic as shown by a relative humidity vs. electrical resistance curve.

Although many efforts have been directed to the concurrent improvement of all of these characteristics, entirely satisfactory results have not been obtained with the conventional humidity sensitive resistors.

Accordingly, a principle object of this invention is to provide a novel and improved humidity sensitive ceramic resistor having a low electrical resistance, high humidity activity and quick response rate to humidity.

A further object of this invention is to provide a novel humidity sensitive ceramic resistor characterized by low electrical resistance, small temperature coefficient of electrical resistance over a wide temperature range, high humidity activity, particularly at low humidity, and a quick response rate to humidity.

A still further object of this invention is to provide a novel humidity sensitive ceramic resistor having a high stability with respect to time, atmosphere, temperature and electric load and which can be produced at low cost.

These objects are achieved according to this invention by providing a humidity sensitive ceramic resistor comprising a ceramic plate having a conducting electrode secured to a surface thereof, the ceramic plate consisting essentially of, as solid ingredients, at least one main component selected from the group consisting of $MgCr_2O_4$, $FeCr_2O_4$, $NiCr_2O_4$, $CoCr_2O_4$, $MnCr_2O_4$, $CuCr_2O_4$, $Mg_2TiO_4$, $Zn_2TiO_4$, $Mg_2SnO_4$ and $Zn_2SnO_4$, and if desired, at least one component selected from the group consisting of $TiO_2$, $ZrO_2$, $HfO_2$ and $SnO_2$. Such a humidity sensitive ceramic resistor provided according to this invention is suitable for use in air conditioners, dew-point protectors, cooking controllers, etc.

Figure 1:
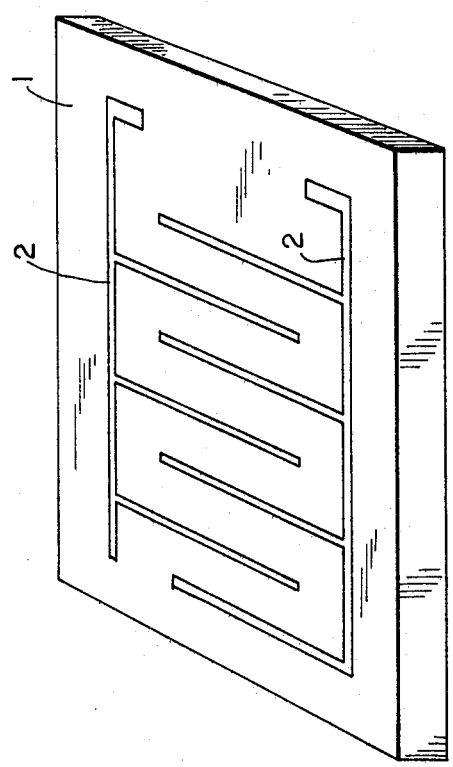
Figure 4:
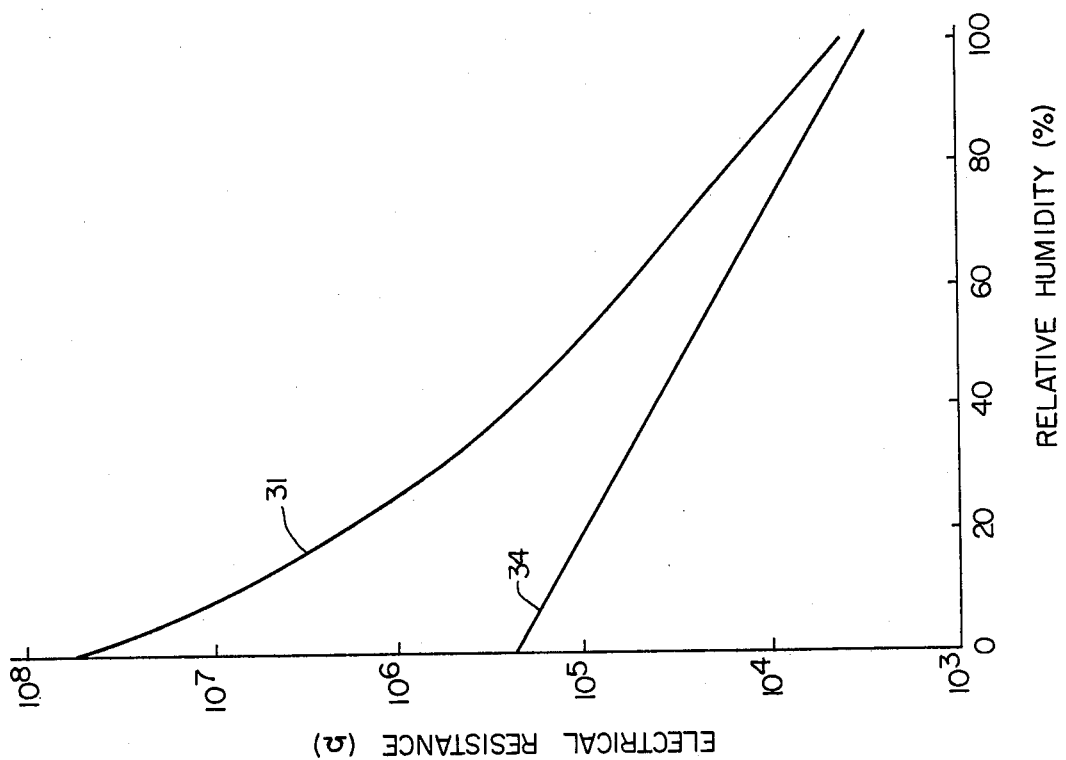
Figure 3:
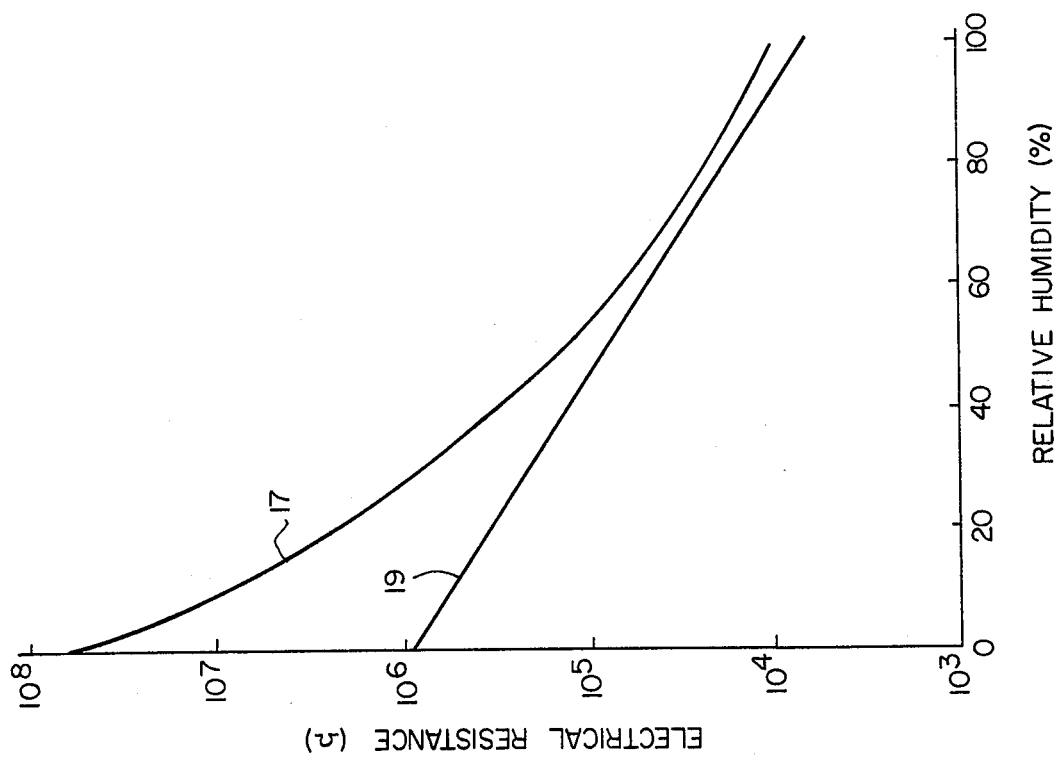

These and other objects and features of this invention will become apparent upon consideration of the following detailed description taken together with the accompanying drawings, in which:

FIG. 1 is a schematic perspective view of a humidity sensitive ceramic resistor of a preferred embodiment of this invention; and FIGS. 2, 3 and 4 are graphs illustrating the electrical resistances at varying relative humidities of the humidity sensitive ceramic resistor shown in FIG. 1.

Before proceeding with the detailed description of this invention, an example of the construction of a humidity sensitive ceramic resistor according to this invention will be explained with reference to FIG. 1, wherein a semiconductive ceramic plate designated by a reference numeral 1 has interdigital electrodes 2 applied to one surface thereof.

In accordance with this invention, it has been discovered that a ceramic plate composed essentially of at least one component with a spinel type cubic symmetry selected from the group consisting of $MgCr_2O_4$, $FeCr_2O_4$, $NiCr_2O_4$, $CoCr_2O_4$, $MnCr_2O_4$, $CuCr_2O_4$, $Mg_2TiO_4$, $Zn_2TiO_4$ $Mg_2SnO_4$ and $Zn_2SnO_4$, and further, if desired, at least one component selected from the group consisting of $TiO_2$, $ZrO_2$, $HfO_2$ and $SnO_2$ (wherein $TiO_2$ is 1 to 99 mole percent and each of $ZrO_2$, $HfO_2$ and $SnO_2$ is 1 to 40 mole percent) has a low electrical resistance, small temperature coefficient of electrical resistance over a wide temperature interval, high humidity activity, quick response rate to humidity and high stability with respect to time, atmosphere, temperature and electric load.

The component oxides are intimately mixed in the desired composition proportions and fired in accordance with a schedule set forth hereinafter for production of a fired ceramic body.

Semiconductive ceramics for humidity sensitive resistors are made in a per se conventional manner with the composition as shown in Tables I and II. The raw materials employed for the ceramics are commercially pure grade MgO, FeO, NiO, CoO, $MnO_2$, CuO, ZnO, $Cr_2O_3$, $SnO_2$, $TiO_2$, $ZrO_2$, and $HfO_2$. It should be noted that any compound which can be converted, upon being fired, to the corresponding oxide can be used as a raw material.

Batches of raw materials are ball milled with water for intimate mixing and then dried. The powder is admixed with an emulsion of polyvinylalcohol in a proportion of 100 grams of the powder to 12 cc of 6 percent aqueous emulsion of polyvinyl alcohol. The powder mixture is then pressed at 750 kg/cm² into rectangular plates of 12 mm × 11 mm in length and 1 mm in thickness. The plates are sintered in air at 1300° C for 2 hours, while being supported on alumina plates. These sintered plates are then provided, on one surface, with interdigital electrodes. Ruthenium oxide paste is fired at 800° C on the plate surface to form electrodes in a per se conventional manner. As a reference, silver electrode is coated thereon with a silver paint.

The temperature coefficient of electrical resistance is obtained by measuring the electrical resistance over a temperature range of 0° C to +100° C in vaccum (a pressure lower than $10^{-5}$ torr), and the variation is expressed by percentages in comparison with the value of 0° C.

Then, humidity properties are measured by a per se well-known method for the resultant humidity sensitive ceramic resistor. Electrical resistance is measured by applying an electric field of 10 V (A.C).

Humidity activity is obtained by measuring electrical resistance over a relative humidity range of 0 percent to 100 percent at 20° C. The activity ($\alpha$) is computed from electrical resistance at a relative humidity of 0 percent ($R_0\%$) and electrical resistance at a relative humidity of 95 percent ($R_{95}\%$).

Response rate to humidity is measured by varying the relative humidity from 0% to 100%.

The load life test is carried out in a thermostat at 80° C and more than 95 percent (relative humidity) by applying a current of 10 milliamperes for 5000 hours, and the variation in the value of $R_0\%$ and $R_{95}\%$ is expressed by the electrical resistance.

According to this invention, it has been discovered that the following base compositions with spinel type structure indicated in Table I can provide high humidity activity materials having, in particular, a humidity activity over a wide relative humidity range of 0% to 100%.

The measured humidity properties of the resultant humidity sensitive ceramic resistors are shown in Table I. As apparent from Table I, the base composition results in a high humidity activity, low electrical resistance, quick response rate to humidity and high stability with respect to time, temperature, humidity and electric load.

The humidity dependence of the electrical resistance of the resultant resistor is shown in FIG. 2. As shown in FIG. 2, the humidity sensitive ceramic resistor according to this invention has nearly linear relative humidity vs. logarithmic electrical resistance characteristics. The example corresponds to $MgCr_2O_4$ base composition (Sample No. 1). The other base compositions exhibit similar characteristics.

It has been further discovered according to this invention that the base compositions can be improved as to the humidity properties as well as the temperature coefficient of the electrical resistance, by combining therewith at least one component selected from the group consisting of $TiO_2$, $ZrO_2$, $HfO_2$ and $SnO_2$, wherein $TiO_2$ is 1 to 99 mole percent, and each of $ZrO_2$, $HfO_2$ and $SnO_2$ is 1 to 40 mole percent.

The ceramic specimens of these compositions show two phases consisting of a spinel type cubic phase and the additional component phase, i.e. $TiO_2$, $ZrO_2$, $HfO_2$ and/or $SnO_2$, wherein the latter phase becomes more pronounced as the additional component increases. Due to the two-phase structure, the ceramic exhibits a smaller temperature coefficient of electrical resistance than the base composition. In the two-phase composition, there is no need for temperature compensation of electrical resistance in controlling humidity at various temperatures.

Moreover, the two-phase composition shows two types of humidity dependence of electrical resistance, depending on the composition ratio; one is a non-linear type, particularly causing a higher humidity activity at the low relative humidity side than the base composition, with an addition of a small amount of the above-mentioned additional component; and the other is a linear type with a combination of the base component and a large amount of the additional component and causes a lower electrical resistance at 0 percent relative humidity than the base composition.

Such humidity sensitive ceramic resistors show the above-mentioned improved properties with the other humidity properties still remaining at a relatively good value. The humidity properties of the humidity sensitive ceramic materials in accordance with this invention are shown in Table II. It is apparent from Table II that the compositions within the range of this invention exhibit excellent humidity properties.

The humidity dependencies of the electrical resistances of resultant resistors are shown in FIGS. 3 and 4, taking Samples 17, 19, 31 and 34 as examples. As apparent from FIGS. 3 and 4, there are two types of ceramic resistors: one type showing non-linear characteristics with a sudden decrease of electrical resistance in the range of low relative humidity i.e. less than 50%; and the other type showing linear characteristics over the range of relative humidity from 0 percent to 100 percent.

Table I

| Sample Number | Ceramic Compsition (mole %) | Humidity Properties | | | Varied Value After Life Test | | Response Rate (second) |
|---|---|---|---|---|---|---|---|
| | | $R_0\%$ ($\Omega$) | $R_{95}\%(\Omega)$ | $\alpha$ | $R_0\%$ ($\Omega$) | $R_{95}\%$ ($\Omega$) | |
| 1 | $MgCr_2O_4$ | $1.0\times10^8$ | $8.0\times10^4$ | $1.3\times10^3$ | $1.2\times10^8$ | $1.5\times10^4$ | 3 |
| 2 | $FeCr_2O_4$ | $8.8\times10^7$ | $1.1\times10^5$ | $8\times10^2$ | $9.0\times10^8$ | $1.3\times10^5$ | 3 |
| 3 | $NiCr_2O_4$ | $9.4\times10^7$ | $8.0\times10^4$ | $1.2\times10^3$ | $1.2\times10^8$ | $1.0\times10^5$ | 4 |
| 4 | $CoCr_2O_4$ | $8.2\times10^7$ | $6.3\times10^5$ | $1.3\times10^2$ | $8.4\times10^8$ | $6.5\times10^5$ | 3 |
| 5 | $MnCr_2O_4$ | $8.0\times10^7$ | $5.0\times10^4$ | $1.6\times10^3$ | $8.6\times10^7$ | $5.2\times10^4$ | 3 |
| 6 | $CuCr_2O_4$ | $9.0\times10^7$ | $6.2\times10^4$ | $1.5\times10^3$ | $9.3\times10^7$ | $6.6\times10^4$ | 5 |
| 7 | $Mg_2TiO_4$ | $1.0\times10^8$ | $2.0\times10^5$ | $5\times10^2$ | $1.3\times10^8$ | $2.6\times10^5$ | 2 |
| 8 | $Zn_2TiO_4$ | $8.2\times10^7$ | $2.1\times10^4$ | $3.9\times10^3$ | $8.6\times10^7$ | $2.3\times10^4$ | 3 |
| 9 | $Mg_2SnO_4$ | $1.3\times10^8$ | $7.5\times10^4$ | $1.7\times10^3$ | $1.4\times10^8$ | $7.7\times10^4$ | 3 |
| 10 | $Zn_2SnO_4$ | $1.0\times10^8$ | $8.6\times10^4$ | $1.2\times10^3$ | $1.2\times10^8$ | $8.8\times10^4$ | 3 |
| 11 | $50MgCr_2O_4$—$50FeCr_2O_4$ | $9\times10^7$ | $7.3\times10^4$ | $1.2\times10^3$ | $9.3\times10^9$ | $7.6\times10^4$ | 3 |
| 12 | $50MgCr_2O_4$—$50NiCr_2O_4$ | $1.0\times10^8$ | $6.5\times10^4$ | $1.5\times10^3$ | $1.2\times10^8$ | $6.7\times10^4$ | 3 |
| 13 | $50Zn_2TiO_4$—$50Zn_2SnO_4$ | $7.8\times10^7$ | $2.5\times10^4$ | $3.1\times10^3$ | $8.1\times10^7$ | $2.7\times10^4$ | 3 |
| 14 | $50Mg_2SnO_4$—$50Zn_2SnO_4$ | $1.3\times10^8$ | $8.0\times10^4$ | $1.6\times10^3$ | $1.5\times10^8$ | $8.3\times10^4$ | 3 |
| 15 | $50MgCr_2O_4$—$50Mg_2SnO_4$ | $1.0\times10^8$ | $6.6\times10^4$ | $1.5\times10^3$ | $1.2\times10^8$ | $6.8\times10^4$ | 3 |

Table II

| Sample Number | Ceramic Composition (mole %) | Temperature Coefficient of Electrical Resistance (%) | Humidity Properties | | | Varied Value After Life Test | | Response Rate (second) |
|---|---|---|---|---|---|---|---|---|
| | | | $R_0\%(\Omega)$ | $R_{95}\%(\Omega)$ | $\alpha$ | $R_0\% (\Omega)$ | $R_{95}\% (\Omega)$ | |
| 16 | $MgCr_2O_4$ | 15.3 | $1.0 \times 10^8$ | $8.0 \times 10^4$ | $1.3 \times 10^3$ | $1.2 \times 10^8$ | $8.5 \times 10^4$ | 3 |
| 17 | $99MgCr_2O_4$—$TiO_2$ | 8.0 | $8.0 \times 10^7$ | $9 \times 10^3$ | $8.0 \times 10^3$ | $9.2 \times 10^7$ | $1.3 \times 10^4$ | 3 |
| 18 | $80MgCr_2O_4$—$20TiO_2$ | 5.2 | $2.0 \times 10^7$ | $3.8 \times 10^3$ | $5.3 \times 10^3$ | $2.1 \times 10^7$ | $4.1 \times 10^3$ | 3 |
| 19 | $40MgCr_2O_4$—$60TiO_2$ | 4.8 | $9.0 \times 10^5$ | $8.5 \times 10^3$ | $1.1 \times 10^2$ | $9.2 \times 10^5$ | $8.7 \times 10^3$ | 2 |
| 20 | $MgCr_2O_4$—$99TiO_2$ | 12.1 | $8.3 \times 10^4$ | $1.7 \times 10^3$ | $4.9 \times 10$ | $8.4 \times 10^4$ | $1.8 \times 10^3$ | 1 |
| *21 | $0.5MgCr_2O_4$—$99.5TiO_2$ | 44.0 | $3.7 \times 10^3$ | $3.2 \times 10^3$ | 1.1 | $3.8 \times 10^4$ | $3.8 \times 10^4$ | 1 |
| 22 | $FeCr_2O_4$—$50TiO_2$ | 5.1 | $1.3 \times 10^6$ | $7.2 \times 10^3$ | $1.8 \times 10^2$ | $1.4 \times 10^6$ | $7.3 \times 10^3$ | 2 |
| 23 | $50NiCr_2O_4$—$50TiO_2$ | 4.6 | $1.2 \times 10^6$ | $7.3 \times 10^3$ | $1.6 \times 10^2$ | $1.3 \times 10^6$ | $7.5 \times 10^3$ | 2 |
| 24 | $50CoCr_2O_4$—$50TiO_2$ | 4.4 | $1.2 \times 10^6$ | $7.3 \times 10^3$ | $1.6 \times 10^2$ | $1.3 \times 10^6$ | $7.4 \times 10^3$ | 2 |
| 25 | $50MnCr_2O_4$—$50TiO_2$ | 5.3 | $1.6 \times 10^6$ | $8.2 \times 10^3$ | $2.0 \times 10^2$ | $1.7 \times 10^6$ | $8.2 \times 10^3$ | 2 |
| 26 | $50CuCr_2O_4$—$50TiO_2$ | 4.8 | $1.3 \times 10^6$ | $8.0 \times 10^3$ | $1.6 \times 10^2$ | $1.5 \times 10^6$ | $8.3 \times 10^3$ | 2 |
| 27 | $50Mg_2TiO_4$—$50TiO_2$ | 4.4 | $1.9 \times 10^6$ | $9.2 \times 10^3$ | $2.0 \times 10^2$ | $2.1 \times 10^6$ | $9.5 \times 10^3$ | 2 |
| 28 | $50Zn_2SnO_4$—$50TiO_2$ | 4.4 | $1.7 \times 10^6$ | $8.5 \times 10^3$ | $2.0 \times 10^2$ | $1.9 \times 10^6$ | $8.6 \times 10^3$ | 2 |
| 29 | $50Mg_2SnO_4$—$50TiO_2$ | 4.4 | $1.6 \times 10^6$ | $8.3 \times 10^3$ | $1.9 \times 10^2$ | $1.8 \times 10^6$ | $8.5 \times 10^3$ | 2 |
| 30 | $50Zn_2SnO_4$—$50TiO_2$ | 4.4 | $1.5 \times 10^6$ | $8.4 \times 10^3$ | $1.8 \times 10^2$ | $1.7 \times 10^6$ | $8.5 \times 10^3$ | 2 |
| 31 | $MgCr_2O_4$—$99SnO_2$ | 6.3 | $6.0 \times 10^7$ | $6 \times 10^3$ | $1.0 \times 10^4$ | $6.2 \times 10^7$ | $6.8 \times 10^3$ | 3 |
| 32 | $10MgCr_2O_4$—$90SnO_2$ | 5.2 | $7.1 \times 10^6$ | $4 \times 10^3$ | $1.8 \times 10^3$ | $7.3 \times 10^6$ | $6.3 \times 10^3$ | 2 |
| 33 | $70MgCr_2O_4$—$30SnO_2$ | 4.4 | $1.3 \times 10^6$ | $5.8 \times 10^3$ | $2.2 \times 10^2$ | $1.4 \times 10^6$ | $6.0 \times 10^3$ | 2 |
| 34 | $60MgCr_2O_4$—$40SnO_2$ | 4.8 | $2.5 \times 10^5$ | $4 \times 10^3$ | $6.3 \times 10$ | $2.7 \times 10^5$ | $4.1 \times 10^3$ | 1 |
| *35 | $55MgCr_2O_4$—$45SnO_2$ | 5.2 | $1.1 \times 10^5$ | $9.2 \times 10^4$ | 1.2 | $1.3 \times 10^5$ | $1.2 \times 10^5$ | 1 |
| 36 | $70MgCr_2O_4$—$30ZnO_2$ | 5.1 | $1.5 \times 10^6$ | $6.2 \times 10^3$ | $2.4 \times 10^2$ | $1.5 \times 10^6$ | $6.4 \times 10^3$ | 2 |
| 37 | $70MgCr_2O_4$—$30HfO_2$ | 5.0 | $1.3 \times 10^6$ | $5.3 \times 10^3$ | $2.5 \times 10^2$ | $1.3 \times 10^6$ | $5.7 \times 10^3$ | 2 |
| 38 | $70FeCr_2O_4$—$30SnO_2$ | 5.2 | $1.3 \times 10^6$ | $5.4 \times 10^3$ | $2.4 \times 10^2$ | $1.4 \times 10^6$ | $5.8 \times 10^3$ | 2 |
| 39 | $70NiCr_2O_4$—$30SnO_2$ | 5.4 | $1.6 \times 10^6$ | $6.2 \times 10^3$ | $2.6 \times 10^2$ | $1.6 \times 10^6$ | $6.6 \times 10^3$ | 2 |
| 40 | $70CoCr_2O_4$—$30SnO_2$ | 5.0 | $1.4 \times 10^6$ | $5.9 \times 10^3$ | $2.4 \times 10^2$ | $1.4 \times 10^6$ | $6.3 \times 10^3$ | 2 |
| 41 | $70MnCr_2O_4$—$30SnO_2$ | 5.0 | $1.4 \times 10^6$ | $5.8 \times 10^3$ | $2.4 \times 10^2$ | $1.5 \times 10^6$ | $6.5 \times 10^3$ | 2 |
| 42 | $70CuCr_2O_4$—$30SnO_2$ | 5.0 | $1.8 \times 10^6$ | $7.1 \times 10^3$ | $2.5 \times 10^2$ | $2.1 \times 10^6$ | $7.7 \times 10^3$ | 2 |
| 43 | $70Mg_2TiO_4$—$30SnO_2$ | 5.0 | $1.6 \times 10^6$ | $6.6 \times 10^3$ | $2.4 \times 10^2$ | $1.6 \times 10^6$ | $7.1 \times 10^3$ | 2 |
| 44 | $70Zn_2TiO_4$—$30SnO_2$ | 5.3 | $1.1 \times 10^6$ | $4.8 \times 10^3$ | $2.3 \times 10^2$ | $1.2 \times 10^6$ | $5.2 \times 10^3$ | 2 |
| 45 | $70Mg_2SnO_4$—$30SnO_2$ | 5.4 | $1.3 \times 10^6$ | $5.6 \times 10^7$ | $2.3 \times 10^2$ | $1.3 \times 10^6$ | $6.1 \times 10^3$ | 2 |
| 46 | $70Zn_2SnO_4$—$30SnO_2$ | 5.0 | $1.4 \times 10^6$ | $6.2 \times 10^3$ | $2.3 \times 10^2$ | $1.4 \times 10^6$ | $6.8 \times 10^3$ | 2 |

*not of this invention

What is claimed is:

1. A humidity sensitive ceramic resistor comprising a ceramic plate having a conducting electrode secured to a surface thereof, said ceramic plate consisting essentially of, as solid ingredients, at least one main component having spinel-type cubic symmetry selected from the group consisting of $MgCr_2O_4$, $FeCr_2O_4$, $NiCr_2O_4$, $CoCr_2O_4$, $MnCr_2O_4$, $CuCr_2O_4$ and, $Mg_2TiO_4$, $Mg_2SnO_4$.

2. A humidity sensitive ceramic resistor according to claim 1, wherein said main component consists essentially of $MgCr_2O_4$.

3. A humidity sensitive ceramic resistor according to claim 1, wherein said main component consists essentially of $FeCr_2O_4$.

4. A humidity sensitive ceramic resistor according to claim 1, wherein said main component consists essentially of $NiCr_2O_4$.

5. A humidity sensitive ceramic resistor according to claim 1, wherein said main component consists essentially of $CoCr_2O_4$.

6. A humidity sensitive ceramic resistor according to claim 1, wherein said main component consists essentially of $MnCr_2O_4$.

7. A humidity sensitive ceramic resistor according to claim 1, wherein said main component consists essentially of $CuCr_2O_4$.

8. A humidity sensitive ceramic resistor according to claim 1, wherein said main component consists essentially of $Mg_2TiO_4$.

9. A humidity sensitive ceramic resistor according to claim 1, wherein said main component consists essentially of $Mg_2SnO_4$.

10. A humidity sensitive ceramic resistor comprising a ceramic plate having a conducting electrode secured to a surface thereof, said ceramic plate consisting essentially of, as solid ingredients, said ceramic plate consisting essentially of, as solid ingredients, 1 to 99 mole percent of at least one component having spinel-type cubic symmetry selected from the group consisting of $MgCr_2O_4$, $FeCr_2O_4$, $NiCr_2O_4$, $CoCr_2O_4$, $MnCr_2O_4$, $CuCr_2O_4$, $Mg_2TiO_4$, $Mg_2SnO_4$ and 99 to 1 mole percent of $TiO_2$.

11. A humidity sensitive ceramic resistor according to claim 10, wherein said component consists essentially of $MgCr_2O_4$.

12. A humidity sensitive ceramic resistor according to claim 10, wherein said component consists essentially of $FeCr_2O_4$.

13. A humidity sensitive ceramic resistor according to claim 10, wherein said component consists essentially of $NiCr_2O_4$.

14. A humidity sensitive ceramic resistor according to claim 10, wherein said component consists essentially of $CoCr_2O_4$.

15. A humidity sensitive ceramic resistor according to claim 10, wherein said component consists essentially of $MnCr_2O_4$.

16. A humidity sensitive ceramic resistor according to claim 10, wherein said component consists essentially of $CuCr_2O_4$.

17. A humidity sensitive ceramic resistor according to claim 10, wherein said component consists essentially of $Mg_2TiO_4$.

18. A humidity sensitive ceramic resistor according to claim 10, wherein said component consists essentially of $Mg_2SnO_4$.

19. A humidity sensitive ceramic resistor comprising a ceramic plate having a conducting electrode secured to a surface thereof, said ceramic plate consisting essentially of, as solid ingredients, 60 to 99 mole percent of at least one main component having spinel-type cubic symmetry selected from the group consisting of $MgCr_2O_4$, $FeCr_2O_4$, $NiCr_2O_4$, $CoCr_2O_4$, $MnCr_2O_4$, $CuCr_2O_4$, $Mg_2TiO_4$, $Mg_2SnO_4$, and 1 to 40 mole percent of at least one additional metal oxide selected from the group consisting of $SnO_2$, $ZrO_2$ and $HfO_2$.

20. A humidity sensitive ceramic resistor according to claim 19, wherein said main component consists essentially of $MgCr_2O_4$.

21. A humidity sensitive ceramic resistor according to claim 19, wherein said main component consists essentially of $FeCr_2O_4$.

22. A humidity sensitive ceramic resistor according to claim 19, wherein said main component consists essentially of $NiCr_2O_4$.

23. A humidity sensitive ceramic resistor according to claim 19, wherein said main component consists essentially of $CoCr_2O_4$.

24. A humidity sensitive ceramic resistor according to claim 19, wherein said main component consists essentially of $MnCr_2O_4$.

25. A humidity sensitive ceramic resistor according to claim 19, wherein said main component consists essentially of $CuCr_2O_4$.

26. A humidity sensitive ceramic resistor according to claim 19, wherein said main component consists essentially of $Mg_2TiO_4$.

27. A humidity sensitive ceramic resistor according to claim 19, wherein said main component consists essentially of $Mg_2SnO_4$.

28. A humidity sensitive ceramic resistor according to claim 19, wherein said additional metal oxide consists essentially of $SnO_2$.

29. A humidity sensitive ceramic resistor according to claim 19, wherein said additional metal oxide consists essentially of $ZrO_2$.

30. A humidity sensitive ceramic resistor according to claim 19, wherein said additional metal oxide consists essentially of $HfO_2$.

* * * * *